United States Patent [19]
Miller et al.

[11] Patent Number: 5,679,362
[45] Date of Patent: Oct. 21, 1997

[54] PACKAGED FUNGAL CULTURE STABLE TO LONG TERM STORAGE

[75] Inventors: David W. Miller, Amherst; Carol Ann Johnson, Worcester; Paul Perry, Acton, all of Mass.

[73] Assignee: EcoScience Corporation, East Brunswick, N.J.

[21] Appl. No.: 270,507

[22] Filed: Jul. 5, 1994

Related U.S. Application Data

[63] Continuation of Ser. No. 109,104, Aug. 19, 1993, abandoned, which is a continuation of Ser. No. 889,594, May 27, 1992, abandoned.

[51] Int. Cl.$^6$ .................................................. A01N 63/04
[52] U.S. Cl. .................. 424/405; 424/84; 424/93.5; 43/132.1
[58] Field of Search ................ 424/93 Q, 405, 424/409, 410, 84, 93.1, 93.5; 43/132.1; 435/240.4, 254, 284, 911

[56] References Cited

U.S. PATENT DOCUMENTS

| | | | |
|---|---|---|---|
| 3,338,794 | 8/1967 | Bladel | 435/39 |
| 3,360,440 | 12/1967 | Haab et al. | 435/34 |
| 3,865,695 | 2/1975 | Massier | 435/254 |
| 4,063,383 | 12/1977 | Green | 47/1.1 |
| 4,097,261 | 6/1978 | Conway | 504/117 |
| 4,235,964 | 11/1980 | Bochner | 435/34 |
| 4,311,477 | 1/1982 | Kitamura et al. | 493/195 |
| 4,390,360 | 6/1983 | Walker | 504/117 |
| 4,530,834 | 7/1985 | McCabe et al. | 424/93.5 |
| 4,718,935 | 1/1988 | Walker et al. | 504/117 |
| 4,724,147 | 2/1988 | Marois et al. | 424/93.5 |
| 4,751,082 | 6/1988 | Schaerffenberg et al. | 424/93.5 |
| 4,765,275 | 8/1988 | Yukawa et al. | 119/15 |
| 4,878,312 | 11/1989 | Shimizu | 47/1.1 |
| 4,886,664 | 12/1989 | Jung et al. | 424/93.4 |
| 4,908,315 | 3/1990 | Kertz | 435/240.4 |
| 4,921,703 | 5/1990 | Higuchi et al. | 424/49 |
| 4,925,663 | 5/1990 | Stimac | 424/9 Q |
| 4,978,505 | 12/1990 | Kertz | 422/66 |
| 5,042,427 | 8/1991 | Bedding | 119/6.7 |
| 5,057,315 | 10/1991 | Gunner et al. | 424/93 Q |
| 5,057,316 | 10/1991 | Gunner et al. | 424/93 Q |
| 5,074,902 | 12/1991 | Connick et al. | 504/117 |
| 5,088,231 | 2/1992 | Kertz | 47/1.01 |
| 5,141,744 | 8/1992 | Chang et al. | 424/93 R |
| 5,238,681 | 8/1993 | Chang et al. | 424/405 |

FOREIGN PATENT DOCUMENTS

| | | |
|---|---|---|
| 0226394 | 6/1987 | European Pat. Off. . |
| A 0 268177 | 5/1988 | European Pat. Off. . |
| A2 202 159 | 5/1974 | France . |
| A 2 480 304 | 10/1981 | France . |
| WOA89 12385 | 12/1989 | WIPO . |
| 9015526 | 12/1990 | WIPO . |
| WO90/15526 | 12/1990 | WIPO . |

OTHER PUBLICATIONS

Smith et al, "The Filamentous Fungi" vol. 4 Fungal Technology, Edward Arnold, Pub. (1983) pp. 328–329, 336–337, 374–375, 376, 378–379.

Patel et al., "Laboratory and Mass Production . . . " Annals of Biology (Ludhiana) 6 (2) pp. 135–140 (1990). Abstract provided. Zimmermann, "The Entomopathogenic Fungus *M. anisopliae* and its Potential as a Biocontrol Agent" Pesticide Science vol. 37 pp. 375–379 (1993).

(List continued on next page.)

*Primary Examiner*—Melvyn I. Marquis
*Assistant Examiner*—Robert H. Harrison
*Attorney, Agent, or Firm*—Arnall Golden & Gregory

[57] ABSTRACT

A method for packaging an insect infection chamber that attracts insects, then infects them with a lethal dosage of fungus, where the packaging maintains high humidity within the chamber, allows fee exchange of gases, and is impermeable to microbes, including fungal spores, viruses, and bacteria.

6 Claims, 4 Drawing Sheets

OTHER PUBLICATIONS

Daoust, et al., "Studies on the Prolonged Storage of *Metarhizium anisopliae* Conidia: Effect of Temperature and Relative Humidity on Conidial Viability and Virulence against Mosquitoes," *J. Invertebrate Pathology* 41, 143–150 (1983).

Reinecke, et al., "BIO 1020, A New Microbial Insecticide for use in Horticultural Crops," *Brighton Crop Protection Conf.—Pests & Diseases* pp. 49–54 (1990).

Ferron, P., "Biological Control of Insect Pests by Entomogenous Fungi," Ann. Rev. Entomol. 23, 409–442 (1978).

Zweig, Gunter, "Environmental Aspects of Controlled Release Pesticide Formulations," *Controlled Release Pesticides* Amer. Chem. Soc., Washington, D.C. 37–53 (1977).

Daoust, et al. "Studies on the Prolonged Storage of *Metarhizium anisopliae* Conidia: Effect of Temperature and Relative Humidity on Conidial Viability and Virulence against Mosquitoes" J. Invertebrate Pathology41, 143–150 (1983).

Daoust, A.R., et al., "Effect of Formulation on the viability of *Metarhizium anisopliae* Conidia," *J. of Invertebrate Pathology*, vol. 41, pp. 151–160 (1983).

Daoust, A.R., et al., "Studies on the Prolonged Storage of *Metarhizium anisopliae* Conidia: Effect on Growth Substrate on Conidial Survival and Virulence Against Mosquitoes," *J. of Invertebrate Pathology*, vol. 41, pp. 161–170 (1983).

Reinecke, W., et al., "BIO 1020, A New Microbial Insecticide for Use In Horticultural Crops," *Brighton Crop Protection Conference—Pests and Diseases*, pp. 49–54 (1990).

Roberts, D.W., et al., "Stability of Entomopathogenic Fungi," *Entomol. Sci Am.* (Misc. Publ.), vol. 10, pp. 19–76 (1977).

Walstad, J.D., "Effects on Environmental Conditions on Two Species of Muscardine Fungi (*Beauveria bassinia* and *Metarhizium anisopliae*)", *J. of Invertebrate Pathology*, vol. 16, 221–226 (1970).

PACKAGED FUNGAL CULTURE STABLE TO LONG TERM STORAGE

This is a continuation of application Ser. No. 08/109,104 filed on Aug. 19, 1993, which is a continuation of U.S. Ser. No. 07/889,594 filed on May 27, 1992, now both abandoned.

BACKGROUND OF THE INVENTION

The present invention relates to an improved means for storing a chamber designed to attract insects and infect them with a lethal dosage of a pathogenic fungus.

There are many varieties of insects that cause major economic losses in agriculture and spread disease among human and other animal populations. The majority of approaches to control of these insects use pesticides. Unfortunately, pesticides are expensive and generally hazardous to the environment, particularly if effective for more than a very short term. Further, there is a tendency among the treated insects for resistant strains to develop, which requires the use of large quantities and different chemicals to treat. The use of chemical insecticides also results in the destruction of non-target biological control agents.

Insect pathogens are a possible alternative to the common use of highly toxic chemical insecticides for the control of insect pests. Fungi are one of the promising groups of insect pathogens suitable for use as biological agents for the control of insects. The most common mode of growth and reproduction for fungi is vegetative or asexual reproduction which involves sporulation followed by germination of the spores. Asexual spores, or conidia, form at the tips and along the sides of hyphae, the branching filamentous structures of multicellular colonies. In the proper environment, the conidia germinate, become enlarged and produce germ tubes. The germ tubes develop, in time, into hyphae which in turn form colonies.

U.S. Pat. Nos. 5,057,316 and 5,057,315 disclose a method for control and extermination of insects, including roaches, flying insects such as the housefly, and other insects such as the adult form of the corn rootworm, by infection of the insects with a fungus that can be pathogenic when administered to the insects in a sufficiently high concentration, by means of an infection chamber. The chamber maintains the spores of a fungus pathogenic to the insects in a viable form, protecting the fungi from the environment (including rain, ultraviolet light and the wind), serves as, or houses, an attractant for the insects, and serves to inoculate the insects with high numbers of spores. The fungal culture provides a continuous supply of spores over a prolonged period of time. The spores attach to the insects and originate germ tubes that penetrate into the insect, which can result in death within three to four days. The chamber design, i.e., shape and color, can be the sole attractants for the insects. Alternatively, food or scents can be used to further enhance the attraction of the insects for the chamber. Although the primary means of infection is by external contact, the insects may also be infected by contact with each other and by ingestion of the spores. In some case, the ingested fungal conidia can also be toxic.

The two most preferred entomopathogenic fungi are *Metarhizium anisopliae* and *Beauveria bassiana*, although other fungi can be used which are pathogenic when the insect is inoculated via the infection chamber. Examples in the patents demonstrate control of *Blatella germanica* (the German cockroach), *Periplaneta americana* (the American cockroach, *Fannia canicularis* (little housefly), *Musca domestica* (housefly), and *Diabrotica undecempunctata* using chambers containing *Metarhizium anisopliae* and *Beauveria bassiana*.

Microbial pesticides have great potential as replacements for chemical pesticides. A historical limitation on the commercial success of insect pathogenic fungi has been their lack of good storage characteristics. Although the chambers described in U.S. Pat. Nos. 5,057,316 and 5,057,315 have been demonstrated to be highly effective both in the laboratory and under actual field test conditions, it is necessary that they withstand shipping and be stable to prolonged storage at room temperature in order to constitute a viable commercial product.

It is therefore an object of the present invention to provide a method and means for increasing the shelf-life of a pathogenic fungus, especially *Metarhizium anisopliae*, on a nutrient medium.

It is a further object of the present invention to provide improved packaging for insect infection chambers utilizing a pathogenic fungus.

It is another object of the present invention to identify the conditions that maximize the infectivity of fungal cultures to insects.

SUMMARY OF THE INVENTION

Conditions are described which allow for the long term storage of the entomopathogenic fungus *Metarhizium anisopliae* and other fungi when present in an infection chamber for the control of insects such as cockroaches. It has been found that when packaged under normal atmospheric gas conditions and at 100% relative humidity (RH), *M. anisoplieae* conidia remain viable at room temperature for an extended period of time. During such storage, there is no detectable loss in the ability of the fungus to infect and cause the death of susceptible insects; efficacy and viability are directly related. Storage materials which are useful in maintaining the necessary condition of high relative humidity, such as polypropylene and low and high density polyethylene, are also described.

DETAILED DESCRIPTION OF THE INVENTION

In U.S. Pat. Nos. 5,057,315 and 5,057,316, the teachings of which are incorporated herein, a method for control and extermination of roaches and other insects using the dissemination of entomopathogenic fungi including, for example, *Metarhizium anisopliae* and *Beauveria bassiana*, was described. The fungi are applied to the environment to be treated using a infection chamber consisting of a closed chamber having entrances for the insects and containing a living culture of a fungus pathogenic to insects. The geometry of the device is such that upon entering the chamber the insects come in contact with an infective dosage of the culture of the pathogenic fungus.

The infection chambers are placed in habitats frequented by the insects. To insure commercial success, a key product characteristic is the stability of the product under standard storage conditions, generally room temperature and those additional conditions that can be maintained by the packaging material. A product should maintain a 'fresh' state for as long a period as possible. In the case of insect pathogenic fungi, this means that the fungus must remain both viable and efficacious (pathogenic) during storage.

It has been discovered that the fungus used in the insect infection chambers stores very poorly at room temperature in the absence of oxygen, regardless of the configuration of the chamber or storage container. The fungal spore, the conidium, is not "inert" but actually consumes significant amounts of oxygen. Without continual access to oxygen, the fungus loses its viability, resulting in a chamber that is not efficacious in lethally infecting insects, although it is possible for the fungus to decline to 1% viability of the conidia in the chamber and still be efficacious. The fungus also has a requirement for high humidity. This is not determined other than as including water vapor and is quantified as 100% relative humidity, in contrast to no added water or 0% humidity. Increasing the storage temperature from room temperature, i.e., 22° to 25° C., up to 42° C. decreases the relative humidity requirements.

To meet both of these requirements, adequate oxygen and high humidity, a packaging material for the insect storage chamber, as well as the fungal cultures in general, has been designed which retains most of the water vapor while allowing free exchange of gases, including oxygen and carbon dioxide. The material is preferably impermeable to microbial organisms, including fungal spores, bacteria, and viruses.

Conditions are now described which allow for a considerable stability period, that is, shelf life, for an insect pathogenic fungus, *Metarhizium anisopliae*. These conditions are achieved by packaging the fungus under atmospheric gas and 100% RH. The packaging material is selected to allow the gases to reach an equilibrium while maintaining 100% RH.

Packaging Material

A variety of materials having defined characteristics with regard to their barrier properties; that is, their ability to contain or allow the movement of differing gases through a layer of the material, are commercially available. These materials come in both rigid and flexible formats. Pouches made of flexible barrier films are readily available in a variety of properties and configurations.

The most preferred material for packaging the chambers is 2 to 8 mil thick low density and high density polyethylene (referring to the extent of branching of the polymer) polyethylene that can be sealed with heat. Other materials include polypropylene, which is slightly less permeable to air than the polyethylene. As shown below, these commercially available materials are characterized by low water vapor transmission but high gas permeability.

TABLE 1

Properties of Packaging Materials

| Material | Water Vapor trans[a] | Gas permeability[b] $O_2$ | $N_2$ | $CO_2$ | Water absorption |
|---|---|---|---|---|---|
| Polyethylene (low density) | 1.3 | 550 | 180 | 2900 | low |
| Polyethylene (high density) | 0.3 | 600 | 70 | 4500 | low |
| Polypropylene | 0.7 | 240 | 60 | 800 | low |

[a]g loss/24 h/100 $in^2$/mil at 95° F., 90% RH.
[b]cc/24 h/100 $in^2$/mil at 77° F., 50% RH; ASTM D1434-63

Other materials that are commercially available can be substituted for the polyethylene and polypropylene to provide equivalent gas and water vapor transfer. These materials can be obtained from D & B Plastics, Fairmouth, Minn., or other supplies of plastic sheeting.

Methods for Packaging the Chambers

The chambers are assembled and sealed within the material using conventional methods known to those skilled in the art, such as heat sealing. Ultrasonic sealing can be used but is not preferred. The chamber is packaged within the smallest bag that will contain the chamber, with no additional air or water being added at the time of sealing, to the extent possible.

The present invention will be further understood by reference to the following non-limiting examples demonstrating the importance of various features of the method and packaging materials.

The following materials and methods were used to determine the effect of various storage conditions on viability and efficacy of the fungal culture.

Viability

Percent viability of *M.anisopliae* (M.a.) conidia was determined using Potato Dextrose Agar (PDA) Plates.

METHODS

For each sample of M.a. conidia:

1. Obtain a fresh, sterile plate of PDA

2. M.a. conidia are collected by gently touching the tip of a small sterile paintbrush to the conidial lawn. Touch brush tip to the inside of a sterile petri dish to remove excess conidia. Only a small amount of conidia are needed.

3. Carefully and gently brush the conidia onto one quarter of the PDA plate, repeat for the other three quarters using conidia obtained from different areas of the M.a. source. One or two brush strokes per quarter is sufficient.

4. Incubate petri dishes at 28° C. for 11–13 hours.

5. After 13 hours of incubation, examine the surface of each inoculated area at 200 power under the compound microscope.

6. Find a field that allows examination of individual conidia. Count at least 200 conidia and record the number of viable and non-viable conidia. A viable conidium has a germ tube at least as long as the diameter of the conidia.

7. For each inoculated quarter obtain the number of viable conidia/total conidia counted, average the four counts together and multiply by 100 to determine the percentage of viable conidia.

Efficacy

Efficacy was determined as described below using *Blatella germanica* in a shoe box bioassay.

MATERIALS

Polystyrene shoe storage boxes (12.5×6.75×3.6 in) having air holes in the top covered with Polyester mosquito mesh netting.

Adult German cockroaches (*B. germanica*; JK-Consulting, Amherst, Mass.), fed PURINA LAB CHOW (Purina #5001; Purina Mills, Inc., St. Louis, Mo.) with free access to distilled water in a test tube stoppered with tissue.

Environmental chamber with controlled temperature and humidity and continuous data recorder (28° C. and 75% RH).

METHODS

Cockroaches

Adult cockroaches were separated into prepared petri plates (having a thin coat of petroleum jelly on the vertical sides) (maximum of 50 adults/plate) containing a pellet of PURINA LAB CHOW™ and a water tube. Petri plates were checked daily. Petri plates of adults were held at 15°±3° until start of the bioassay.

Bioassay Set-up

Vertical sides of shoe boxes were coated with a thin layer of petroleum jelly. A pellet of autoclaved PURINA LAB CHOW™ and a water tube were added to each shoe box. Twenty cockroaches were added to each box. The shoe boxes of cockroaches were placed in the environmental chamber. One infection chamber was added to each of four shoe boxes of cockroaches. Four additional shoe boxes were used as controls.

Incubation

Shoe boxes of cockroaches were incubated at 28°±3° C. and 75°±15% RH under a 10 hour photoperiod. Cockroach mortality was recorded weekly for 6 weeks. The criteria for 'dead' was if no movement was observed when the insect was prodded with a blunt instrument.

EXAMPLE 1

Loss of fungal viability when chambers are left unprotected at room temperature and with uncontrolled humidity Chambers from four different batches of fungus were placed inside a cabinet at room temperature and humidity. At intervals measured in days, chambers were sampled and the viability of the fungus determined.

Figure 1A:
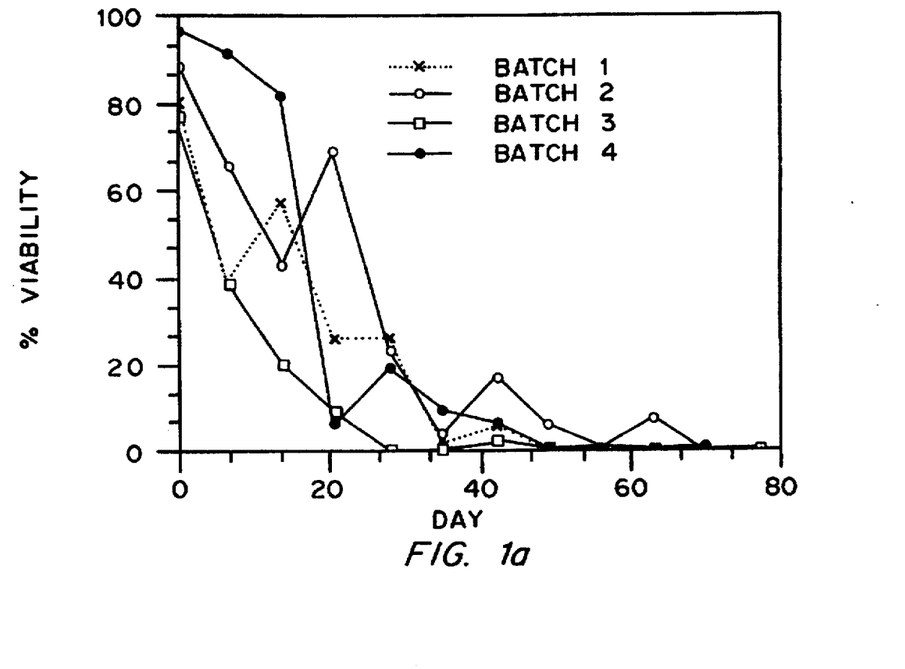
FIG. 1a is a graph of % viability of fungus within the infection chambers incubated under uncontrolled conditions over time (days), for four batches of *Metarhizium anisopliae*.

The results shown in FIG. 1a indicate that fungus loses viability when stored unprotected over any significant period of time.

EXAMPLE 2

Effect on fungal viability when chambers are stored under anaerobic conditions

Five infection chambers were placed in each of a series of one quart mason jars which can be fitted with an air tight lid. For those chambers which were the controls and exposed to atmospheric conditions, the jar lid was left loose. For those chambers which were to be exposed to anaerobic conditions, an Ageless™ (Mitsubishi) oxygen scavenger pack was introduced and the jar lid was tightened down. An Ageless™ pack consists of finely divided un-oxidized iron filings which when exposed to air will begin to oxidize. When this occurs in a sealed environment, such as these jars, all oxygen is removed, creating an anaerobic environment.

Figure 1B:
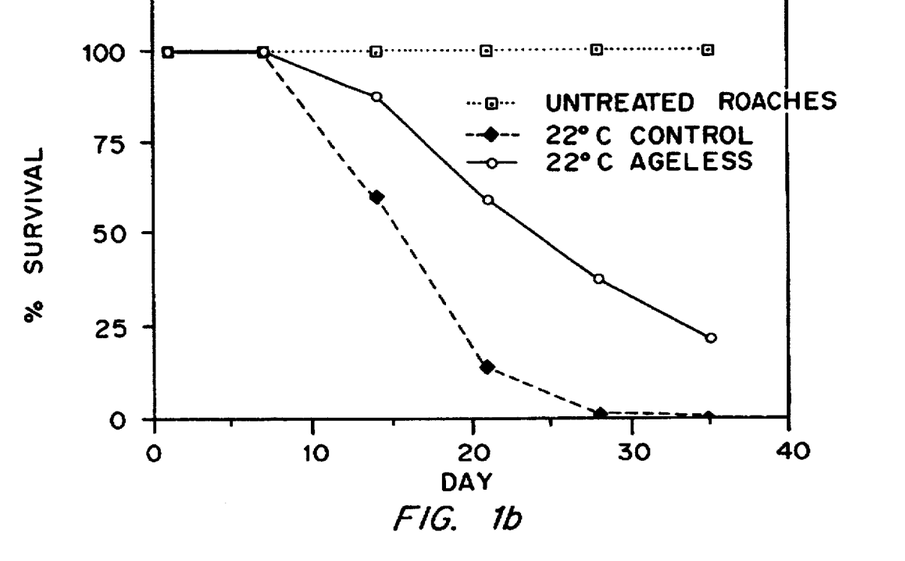
FIG. 1b is a graph of the % survival of roaches exposed to infection chambers containing fungus which had been stored under aerobic (—dark diamonds—) or anaerobic (—O—) conditions over time (days). Survival of roaches not exposed to fungus are shown as (•••open squares•••).

The data shown in Table 2 and FIG. 1b illustrate the average viability as well as the efficacy of the infection chambers after storage for 42 days under these conditions. The results demonstrate that oxygen is a requirement for successful long term storage of the fungus at room temperature.

TABLE 2

Viability of Fungus Inside Infection Chamber.

|  |  | % Viability |
|---|---|---|
| 14 days | Control | 72.06 |
|  | Ageless | 69.94 |
| 42 days | Control | 81.54 |
|  | Ageless | 7.00 |

EXAMPLE 3

Determination of suitable packaging materials for fungus, allowing flux of oxygen Several materials were tested to determine how the live fungus within the infection chamber consumes oxygen and how, when the fungus is packaged, different packaging materials do or do not allow the passage of oxygen, mitigating the oxygen deficit.

Two studies were performed

1) Six chambers with fungus were placed into either (a) a RUBBERMAID™ container (7.5 in×7.5 in×2.75 in), (b) and a 4 mil (0.004 in) low density polyethylene pouch (LDPE) (D&B Plastics, Fairmouth, Minn.), or c) an 8 mil LDPE pouch. There were duplicate samples of each, "A" and "B". While RUBBERMAID™ containers are made of thick polypropylene, a low oxygen permeable material, oxygen transfer can occur around the seal of the lid to the container. LDPE is noted for its low water vapor permeability characteristics and its high oxygen and carbon dioxide permeability characteristics, as shown in Table 1.

The packaged chambers were stored at 30° C. for fourteen days. At the end of this period, the oxygen and carbon dioxide content of the package interiors was sampled using a SERVOMEX™ Company, Norwood, Mass., gas analyzer. The average viability of the fungus within the chambers was then determined. The results are shown in Table 3.

TABLE 3

Conditions inside Packages with Infection Chambers after 14 Days at 30° C.

|  |  | % $O_2$ | % $CO_2$ | % Viability |
|---|---|---|---|---|
| Rubbermaid ™ | A | 16.0 | 5.5 | 95.0 |
|  | B | 11.4 | 10.4 | 92.2 |
| 4 mil LDPE | A | 12.5 | 2.2 | 86.3 |
|  | B | 12.3 | 2.3 | 86.1 |
| 8 mil LDPE | A | 5.9 | 3.8 | 93.0 |
|  | B | 5.0 | 4.0 | 94.1 |

2) Twelve chambers were sealed inside each of several foil laminate pouches (Laminated Foil and Packaging, Portsmouth, N.H.). The laminations were polyethylene-aluminum foil (0.0007 in)-polyethylene; this packaging material is considered completely impermeable to any gas or vapor. The pouches were stored and their oxygen and carbon dioxide levels were subsequently measured. There were duplicate pouches for each sampling point.

The results are shown in Table 4 and demonstrate that all of the oxygen was consumed and carbon dioxide was produced in abundance. The average viability of the fungus was then determined.

TABLE 4

Conditions inside Foil Pouches after Three Months.

|  |  | % O$_2$ | % CO$_2$ | % Viability |
|---|---|---|---|---|
| 22° C. | A | 0.3 | 23.4 | 15.0 |
|  | B | 0 | 22.9 | 11.15 |
| 30° C. | A | 0 | 23.7 | 0.0 |
|  | B | 0 | 22.0 | 0.25 |

The results of these two experiments demonstrate the extent of oxygen consumption by the fungus, and, when combined with the other examples, demonstrate the importance of providing the appropriate packaging. Fungus with access to oxygen remains viable.

EXAMPLE 4

Importance of high humidity on storage stability of the fungus

Five infection chambers with fungus were placed inside each of a series of RUBBERMAID™ containers to determine the role that the relative humidity (RH) within the container had on the long term storage stability of the fungus. One series of containers had placed inside of them a wet sponge to insure the container atmosphere was kept at 100% RH. Another series of containers had a saturated solution of magnesium chloride (MgCl$_2$) placed within to maintain 30% RH. A final series of containers was kept at 0% RH by placing inside Of them a large amount of silica gel. All of the containers were stored at room temperature and the infection chambers within sampled periodically to determine fungal viability and chamber efficacy over an extended period of time.

Figure 2:
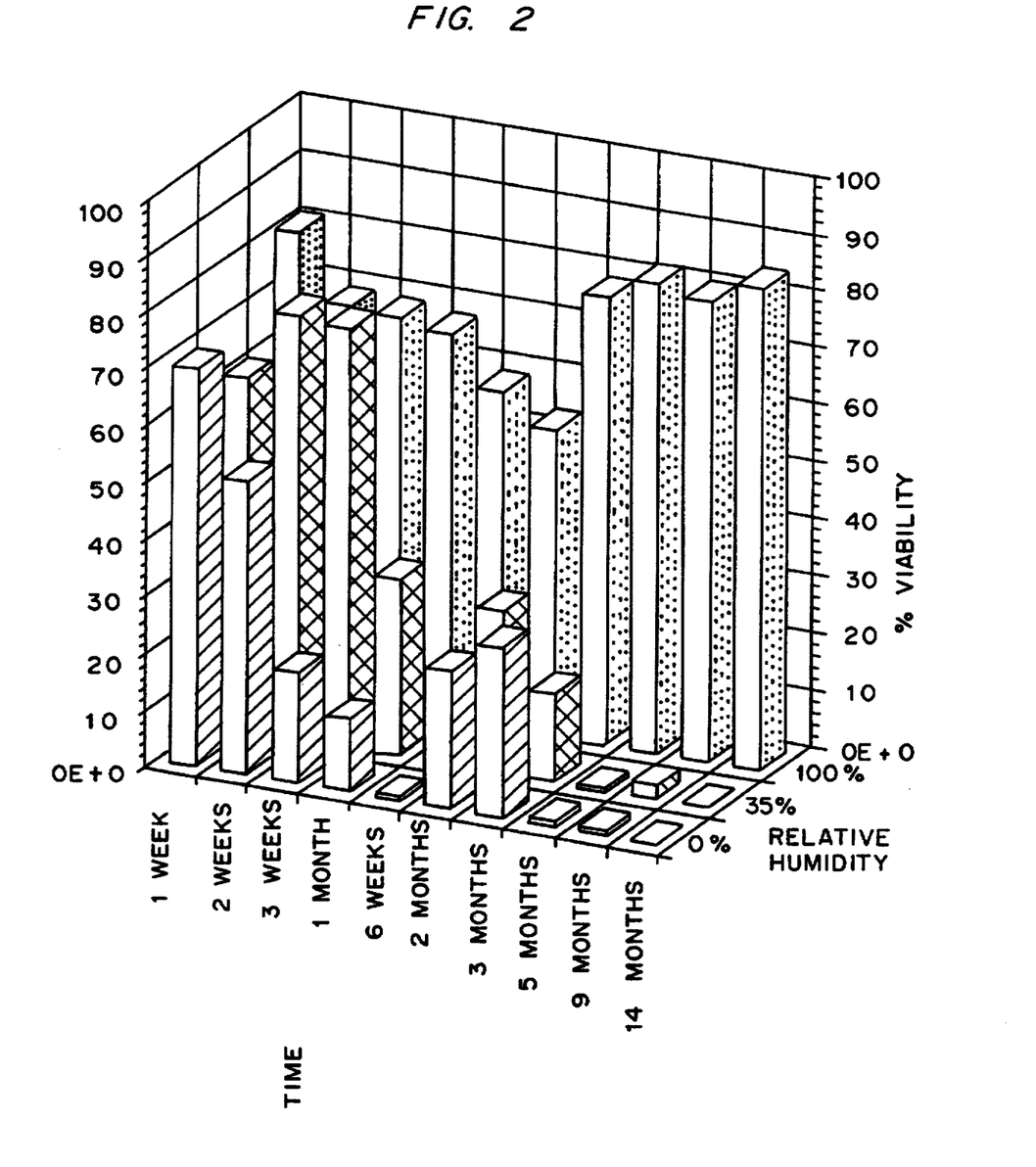
FIG. 2 is a three dimensional graph of the viability of fungus within infection chambers inubated at different relative humidities: % viability versus % relative humidity versus time.
Figure 3:
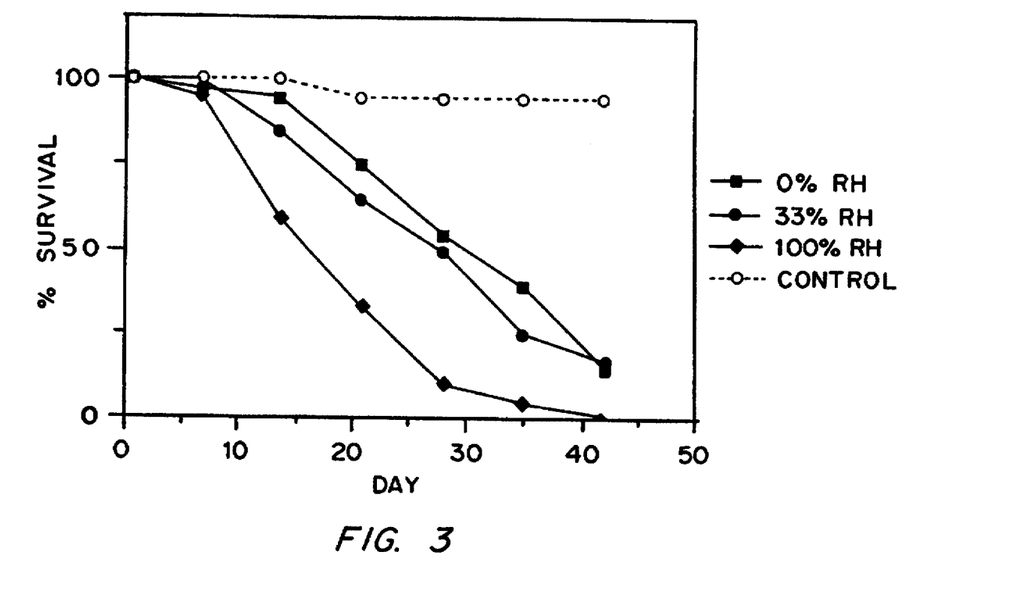
FIG. 3 is a graph of % survival of cockroaches (*Blatella germanica*) over time (days) exposed to infection chambers containing *Metarhizium anisopliae* cultures, stored at 0% RH (dark squares), 33% RH (dark circles), 100% RH (dark diamonds), and controls (open circles) at 22° C.
Figure 4A:
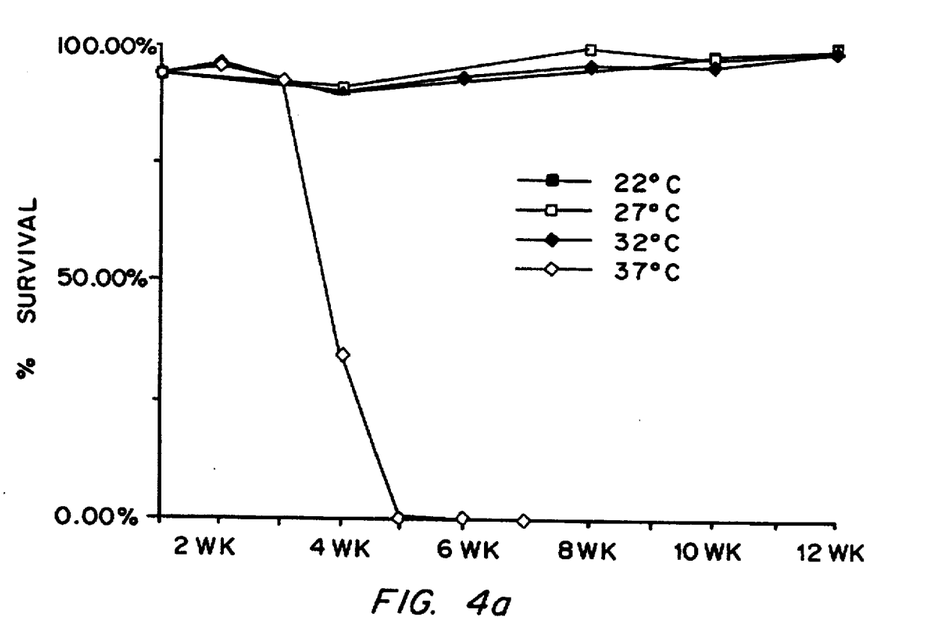
FIGS. 4a, 4b, and 4c are graphs of the % survival over time (weeks) for *M. anisopliae* strain ESF 53 (FIG. 4a), *M. anisopliae* strain ESF 1 (FIG. 4b), and *Beauveria bassiana* strain ESF 2 (FIG. 4c) at 22° C. (dark squares), 27° C. (open squares), 32° C. (dark diamonds), and 37° C. (open diamonds).
Figure 4B:
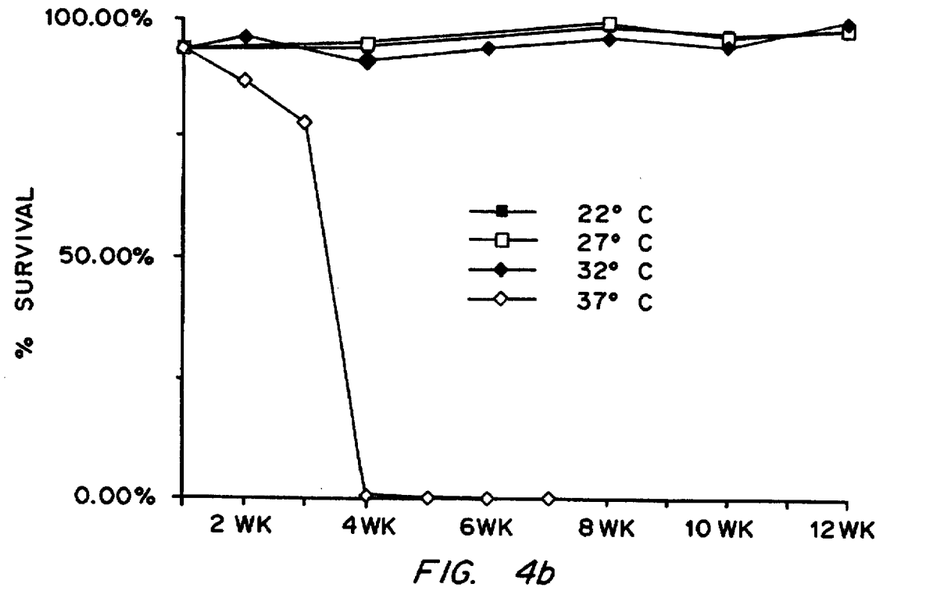
Figure 4C:
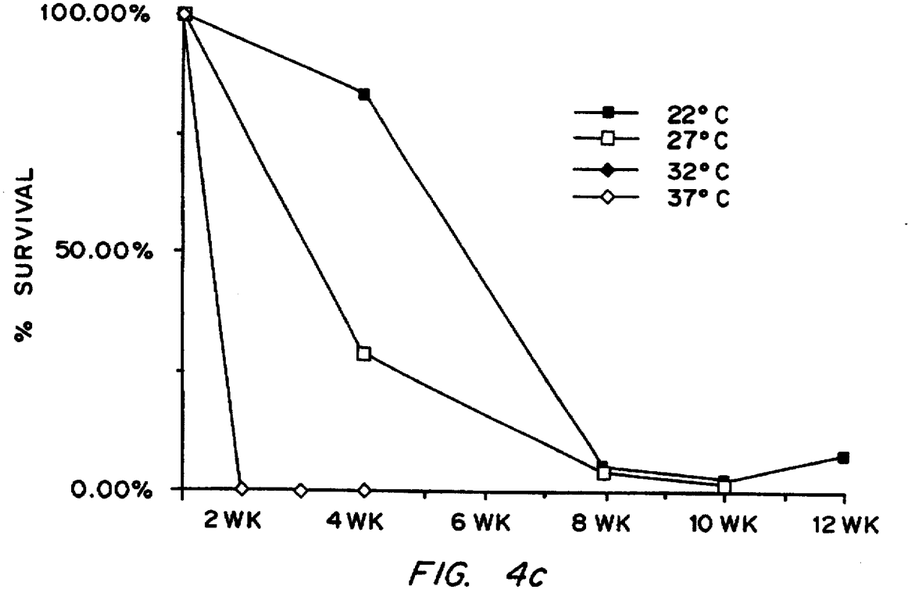

The results are shown in Table 5 and in FIG. 2 and demonstrate the average measured viability in tabular and graph form through 14 months of storage. The efficacy of the infection chambers at 9 months is also shown in FIG. 3.

The results demonstrate that 100% RH is significantly better than other humidities for the successful long term storage of the fungus.

TABLE 5

Percentage Viability at Various Relative Humidities.

| | Relative Humidity of | | |
|---|---|---|---|
| Time | 100% | 33% | 0% |
| 1 week | 81 | 61.1 | 69.1 |
| 2 weeks | 69 | 74 | 51 |
| 3 weeks | 68.5 | 73.1 | 19.2 |
| 1 month | 67.3 | 30.5 | 12.7 |
| 6 weeks | 58.4 | 11.4 | 0.54 |
| 2 months | 53.5 | 28 | 23.9 |
| 3 months | 78.3 | 15.3 | 29.8 |
| 6 months | 82.33 | 0.08 | 0.74 |
| 9 months | 80.54 | 2.33 | 0.75 |
| 14 months | 84.29 | 0 | 0 |

EXAMPLE 5

Comparison of different commercial packaging materials in their ability to provide suitable long term storage conditions for the fungus Twelve infection chambers were placed into each pouch of two series of pouches. One pouch series was 8 mil LDPE.

The other pouch series was a foil laminate as in example 3. Pouches were stored at 22° C. or 30° C. The required 100% RH within the pouch was provided by the agar growing medium of the fungus which remains within the chamber after development of the fungus. At periodic intervals the pouches were removed from their storage conditions and initially sampled for gas content. Each sample consisted of duplicate pouches (A and B). The results obtained were consistent with the data obtained in Example 3; that is, within a short period of time, there was no oxygen remaining in the foil laminate pouches but there was a substantial amount within the LDPE pouches. The pouches were then opened and the chambers within were sampled for viability of the fungus. The results are attached and show that at three months, a clear distinction emerges between an oxygen permeable (LDPE) pouch and an oxygen impermeable (foil) pouch.

It can be concluded that the fungus requires oxygen and that a LDPE bag allows sufficient exchange to maintain the viability of the fungus over long term storage.

TABLE 6A

Conditions within Foil Pouch at Three Months.

| | | % $O_2$ | % $CO_2$ | % Viability |
|---|---|---|---|---|
| 22° C. | A | 0.3 | 23.4 | 15.00 |
| | B | 0 | 22.5 | 11.15 |
| 30° C. | A | 0 | 23.7 | 0.00 |
| | B | 0 | 22.0 | 0.00 |

TABLE 6B

Conditions within LDPE Pouch at Three Months

| | | % $O_2$ | % $CO_2$ | % Viability |
|---|---|---|---|---|
| 22° C. | A | 8.5 | 3.0 | 92.1 |
| | B | 8.8 | 2.5 | 90.9 |
| 30° C. | A | 8.7 | 3.0 | 86.0 |
| | B | 4.5 | 4.2 | 87.8 |

EXAMPLE 6

Comparison of Packaging Conditions on Viability of Different Fungi

FIGS. 4*a*, *b* and *c* demonstrate the percent survival over time for three different fungi stored under conditions as described in Example 3. Strain ESF 2 is a *Beauveria bassiana* strain and strains ESF i and ESF 53 are strains of *Metarhizium anisopliae* strains.

Under the same conditions, the *Beauveria bassiana* does not survive well using the same packaging material that perserves both *Metarhizium anisopliae* strains. These results indicate that it is not possible to extrapolate from data on packaging of other types of microorganisms to fungi with respect to the efficacy of the packaging in promoting survival of fungi.

Modifications and variations of the methods and materials for packaging insect contamination chambers will be obvious to those skilled in the art from the foregoing detailed description. Such modifications and variations are intended to come within the scope of the appended claims.

We claim:

1. A packaged fungal culture comprising fungal spores consisting of viable pathogenic Metarhizium spores, wherein the spores and sufficient water to create an atmosphere of 100% relative humidity are packaged within a sealed flexible packaging material wherein the packaging material allows free exchange of $O_2$ and $CO_2$, has low permeability to water vapor and maintains 100% relative humidity around the spores, and is impermeable to microbial organisms.

2. The culture of claim 1 wherein the packaging material is a flexible membrane between 2 and 8 mils in thickness.

3. The culture of claim 2 wherein the packaging material is selected from the group consisting of low density polyethylene, high density polyethylene, and polypropylene.

4. The culture of claim 1 wherein the fungal spores are in an infective chamber which is attractive for insects and designed to infect the insects with a lethal dosage of fungal spores when the insects enter the chamber.

5. The culture of claim 1 wherein the fungal spores are produced by *Metarhizium anisopliae*.

6. The culture of claim 4 wherein the infective chamber includes a nutrient media for growing the fungal spores.

* * * * *